US00RE43617E

(19) United States
(12) Reissued Patent
Andrew et al.

(10) Patent Number: US RE43,617 E
(45) **Date of Reissued Patent: *Aug. 28, 2012**

(54) TISSUE LIQUEFACTION AND ASPIRATION

(76) Inventors: Mark S. Andrew, Haddonfield, NJ (US); Mylina Andrew, Haddonfield, NJ (US)

( * ) Notice: This patent is subject to a terminal disclaimer.

(21) Appl. No.: 12/030,694

(22) Filed: Feb. 13, 2008

Related U.S. Patent Documents

Reissue of:

(64) Patent No.: 7,011,644
Issued: Mar. 14, 2006
Appl. No.: 10/752,798
Filed: Jan. 7, 2004

U.S. Applications:

(60) Continuation-in-part of application No. 10/408,604, filed on Apr. 7, 2003, now Pat. No. 6,676,629, which is a continuation-in-part of application No. 09/030,792, filed on Feb. 26, 1998, now Pat. No. 6,544,211, which is a continuation-in-part of application No. 08/823,713, filed on Mar. 25, 1997, now Pat. No. 6,074,358, which is a division of application No. 08/384,655, filed on Feb. 6, 1995, now Pat. No. 5,616,120.

(51) Int. Cl.
*A61M 1/00* (2006.01)

(52) U.S. Cl. ..... 604/27; 604/113; 433/215

(58) Field of Classification Search ..... 604/28, 604/35, 43, 113; 606/107; 433/32, 80, 215
See application file for complete search history.

(56) References Cited

U.S. PATENT DOCUMENTS

| | | | | |
|---|---|---|---|---|
| 3,247,851 | A | | 4/1966 | Seibert |
| 3,351,063 | A | | 11/1967 | Malaker et al. |
| 3,589,363 | A | | 6/1971 | Banko et al. |
| 3,624,907 | A | | 12/1971 | Brass et al. |
| 3,693,613 | A | | 9/1972 | Kelman |
| 3,906,954 | A | | 9/1975 | Baehr et al. |
| 3,930,505 | A | * | 1/1976 | Wallach ..... 604/22 |
| 4,019,514 | A | | 4/1977 | Banko |
| 4,078,564 | A | | 3/1978 | Spina et al. |
| 4,135,516 | A | | 1/1979 | Spina et al. |
| 4,191,176 | A | | 3/1980 | Spina et al. |
| 4,215,476 | A | | 8/1980 | Armstrong |
| 4,386,927 | A | | 6/1983 | Eichenbaum |
| 4,411,652 | A | | 10/1983 | Kramer et al. |
| 4,496,342 | A | | 1/1985 | Banko |
| 4,597,388 | A | | 7/1986 | Koziol et al. |

(Continued)

FOREIGN PATENT DOCUMENTS

EP 0485133 5/1992

(Continued)

OTHER PUBLICATIONS

Litigation Search for USPN 7011644, Jun. 23, 2011.*

(Continued)

*Primary Examiner* — Mark W Bockelman
(74) *Attorney, Agent, or Firm* — Proskauer

(57) ABSTRACT

A method and apparatus are disclosed for liquefying target tissue within a body and aspirating the same while leaving non-target tissue intact. A biocompatible fluid is heated and contacted with target tissue so that the target tissue is melted while non-target tissue remains intact. As the target tissue is being melted it is also aspirated from the body.

28 Claims, 1 Drawing Sheet

U.S. PATENT DOCUMENTS

| | | | | | |
|---|---|---|---|---|---|
| 4,650,461 | A | | 3/1987 | Woods | |
| 4,694,828 | A | | 9/1987 | Eichenbaum | |
| 4,744,360 | A | | 5/1988 | Bath | |
| 4,764,165 | A | | 8/1988 | Reimels et al. | |
| 4,784,649 | A | * | 11/1988 | Imonti et al. | 604/240 |
| 4,804,364 | A | | 2/1989 | Dieras et al. | |
| 4,817,599 | A | | 4/1989 | Drews | |
| 4,857,063 | A | * | 8/1989 | Glenn | 604/317 |
| 4,869,715 | A | | 9/1989 | Sherburne | |
| 4,883,426 | A | * | 11/1989 | Ferrer | 433/91 |
| 4,886,491 | A | | 12/1989 | Parisi et al. | |
| 4,924,863 | A | | 5/1990 | Sterzer | |
| 4,950,267 | A | | 8/1990 | Ishihara et al. | |
| 4,995,880 | A | | 2/1991 | Galib | |
| 5,022,413 | A | | 6/1991 | Spina, Jr. et al. | |
| 5,061,255 | A | | 10/1991 | Greenfeld et al. | |
| 5,169,396 | A | | 12/1992 | Dowlatshahi et al. | |
| 5,222,953 | A | | 6/1993 | Dowlatshahi | |
| 5,257,988 | A | | 11/1993 | L'Esperance, Jr. | |
| 5,324,319 | A | | 6/1994 | Mason et al. | |
| 5,451,208 | A | | 9/1995 | Goldrath | |
| 5,540,679 | A | | 7/1996 | Fram et al. | |
| 5,607,420 | A | | 3/1997 | Schuman | |
| 5,649,923 | A | | 7/1997 | Gregory et al. | |
| 5,653,692 | A | | 8/1997 | Masterson et al. | |
| 6,074,358 | A | | 6/2000 | Andrew et al. | |
| 6,224,378 | B1 | | 5/2001 | Valdes et al. | |
| 6,319,222 | B1 | | 11/2001 | Andrew et al. | |
| 6,440,103 | B1 | | 8/2002 | Hood et al. | |
| 6,497,572 | B2 | | 12/2002 | Hood et al. | |
| 6,544,211 | B1 | * | 4/2003 | Andrew et al. | 604/28 |
| 6,676,629 | B2 | | 1/2004 | Andrew et al. | |
| 2002/0188280 | A1 | | 12/2002 | Nguyen et al. | |
| 2003/0120199 | A1 | | 6/2003 | Sussman et al. | |
| 2006/0100606 | A1 | | 5/2006 | Dobak | |
| 2006/0224154 | A1 | | 10/2006 | Shadduck et al. | |

FOREIGN PATENT DOCUMENTS

| | | |
|---|---|---|
| WO | 90/05493 | 5/1990 |
| WO | 0176518 | 10/2001 |
| WO | 2004037095 | 5/2004 |
| WO | 2007087404 | 8/2007 |
| WO | 2008134713 | 11/2008 |

OTHER PUBLICATIONS

Product Information for the Smith & Nephew Versajet Hydrosurgery, 2004.

Product Information for the Human med Body-Jet, Jul. 2004.

* cited by examiner

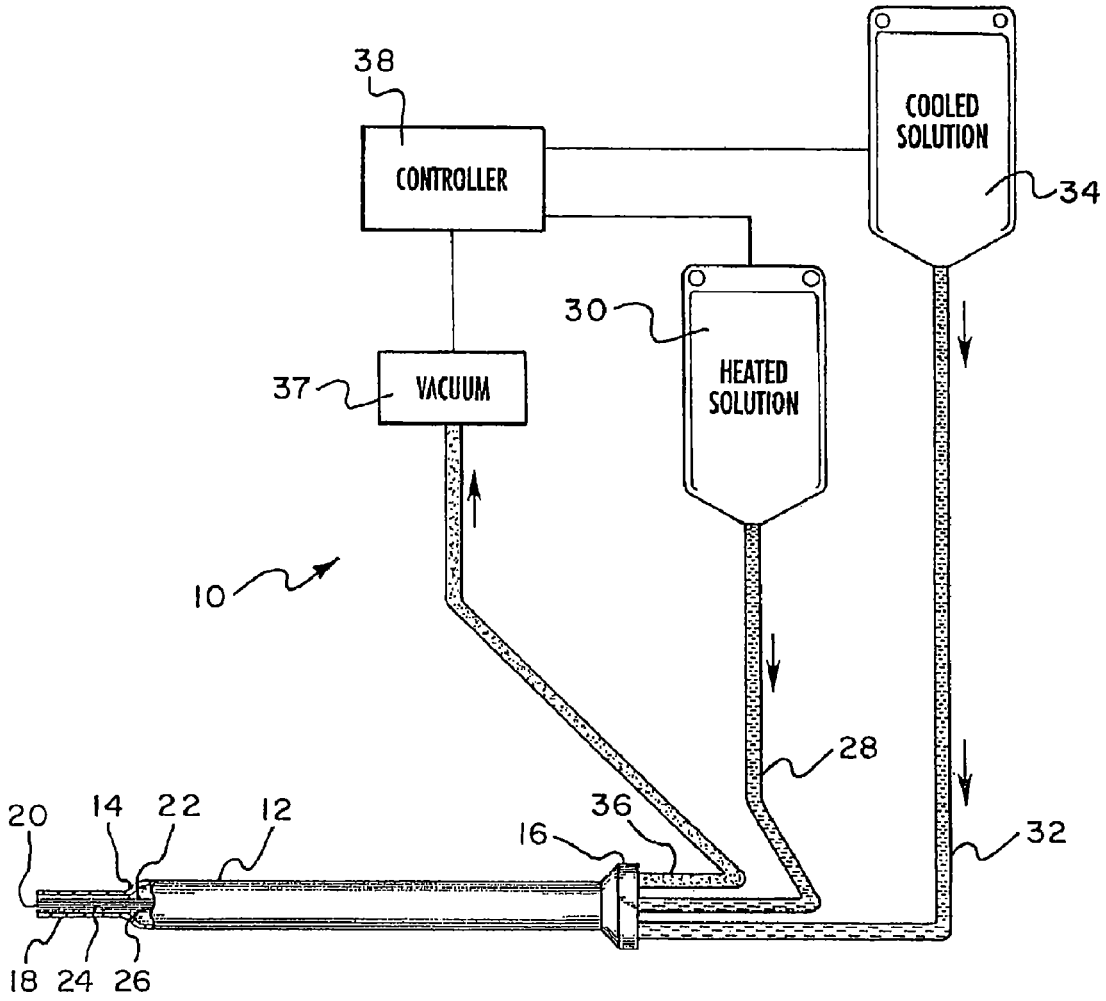
38
CONTROLLER
COOLED SOLUTION
34
30
HEATED SOLUTION
37
VACUUM
10
28
20
14
22
12
36
16
32
18
24
26

TISSUE LIQUEFACTION AND ASPIRATION

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part of U.S. patent application Ser. No. 10/408,604, filed Apr. 7, 2003, now U.S. Pat. No. 6,676,629 which is a continuation-in-part of U.S. patent application Ser. No. 09/030,792, filed Feb. 26, 1998, now U.S. Pat. No. 6,544,211, which is a continuation-in-part of U.S. application Ser. No. 08/823,713, filed Mar. 25, 1997, now U.S. Pat. No. 6,074,358, which is a division of U.S. application Ser. No. 08/384,655, filed Feb. 6, 1995, now U.S. Pat. No. 5,616,120.

BACKGROUND OF THE INVENTION

The present invention is directed toward a method for liquefying target tissue within a body and more particularly, toward a method of heating a biocompatible fluid and presenting such to target tissue, thereby liquefying the target tissue and aspirating it while leaving non-target tissue intact.

Prior thermal energy sources used in surgery have been "dry-heat" devices. Some examples are: thermal lasers, ultrasound, microwave, radio frequency, and electrosurgery devices. These dry-heat energy sources transfer heat from a surgical instrument to a tissue primarily by the heat transfer modalities of conduction and radiation. Thermal lasers, ultrasound, and microwave energy sources can liquefy tissue, but only at very high energy levels. If any of these dry-heat energy sources are placed in direct contact with target surgical tissue, there is no tissue differentiation. That is, healthy as well as unhealthy tissue will be liquefied. For example, collapsing cavitation bubbles in front of an ultrasound surgical instrument release a thermal energy of 13,000° F. per bubble. With such a high thermal energy input there is no differentiation of tissue within the surgical tissue field. That is, all tissue target and non-target, within the target field melts or liquefies. The thermal energy in thermal lasers and ultrasound is inherently high, so the heat cannot be "turned down" or reduced. In microwave, radio frequency, and electrosurgery the level of thermal energy may be reduced but in so doing, liquefaction of tissue is not achieved at all. Rather, cauterization or coagulation of the tissue results.

U.S. Pat. No. 4,924,863 discloses a method for removing artherosclerotic plaque from a patient by heating the plaque under pressure for a limited period of time. When the plaque is heated, it liquefies without causing immediate death of the underlying tissue. The liquefied plaque is then aspirated from the body through a catheter. The means used for heating the plaque is microwave or radio frequency energy. As discussed above, however, in an effort to control the level of energy being produced, all of the plaque may not liquefy.

U.S. Pat. No. 5,540,679 discloses the use of a balloon catheter for heating tissue in a patient's body. A heating device is located within the balloon and is arranged for heating fluid inside the balloon. When the fluid is heated, unwanted tissue, such as a tumor or an enlarged prostate gland, is heated by thermal conduction from the fluid through a wall of the balloon. The heat destroys the tissue which is eventually absorbed into the patient's body. This method uses conduction and as explained above, such a method creates such a high level of energy that there is no tissue differentiation. As a result, healthy tissue may be heated and ultimately destroyed.

U.S. Pat. No. 4,886,491 discloses a method of liposuction using an ultrasonic probe. An ultrasonic probe tip is vibrated at a high frequency and a low amplitude. This method separates the fatty tissue and creates heat which melts some of the fatty tissue. A saline irrigating solution is applied to the area which emulsifies the melted fatty tissue. The emulsified solution is then aspirated. Again, because of the high thermal energy input into the system there is no differentiation of tissue into target and non-target tissue.

SUMMARY OF THE INVENTION

The present invention is designed to overcome the deficiencies of the prior art discussed above. It is an object of this invention to provide a method for liquefying target tissue within a living body while leaving non-target tissue intact, and aspirating the liquefied tissue as it is liquefied.

It is another object of the invention to provide a method for liquefying target tissue by heating a biocompatible fluid and presenting the same to the target tissue.

It is a further object of the invention to provide a method for liquefying fatty tissue and aspirating the same from a patient.

In accordance with the illustrative embodiments, demonstrating features and advantages of the present invention, there is provided a method for liquefying target tissue within a human body. The method includes heating a biocompatible fluid, presenting this fluid to the target tissue which liquefies the tissue, while leaving non-target tissue intact, and aspirating the liquefied tissue as soon as it is liquefied.

The present invention discloses a novel energy source which allows for efficient, safe, minimally invasive, and cost-effective surgery for surgical procedures where the goal of the surgery is to remove unwanted tissue from the body, within a surgical tissue field. The present invention also allows for the differentiation of target tissue from non-target tissue. In other words, the surgical tissue field is defined as the actual anatomical landscape with which the surgeon is physically interacting. Surgical tissue fields are comprised of multiple homogeneous tissue groups. Each of these homogeneous tissue groups has its own melting point. With the present invention, the melting point of a particular tissue group or unwanted tissue is determined in order to liquefy the tissue and rid the patient of the same.

Other objects, features, and advantages of the invention will be readily apparent from the following detailed description of a preferred embodiment thereof taken in conjunction with the drawings.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

The sole FIGURE is an elevational view of a liquefaction and aspiration device of the present invention.

DETAILED DESCRIPTION OF THE PREFERRED EMBODIMENT

Referring now to the drawing in detail, there is shown in the FIGURE a liquefaction and aspiration device constructed in accordance with the principles of the present invention and designated generally as 10.

The liquefaction device 10 includes a hollow handpiece 12 with a first end 14 and a second end 16. An elongated cannula 18 extends from the first end 14 of the handpiece 12 and terminates in a tip 20. The tip 20 has three ports formed therethrough. Three lumens 22, 24, and 26 are positioned in the cannula. Each of the lumens has one end communicating with a corresponding port and an opposite end extending into the handpiece 12.

An irrigation tube 28 has one end thereof connected to the lumen 24 and an opposite end connected to a fluid source 30. The fluid source is heated by a heating element (not shown) that can be located within or outside of the handpiece 12. The heated fluid source 30 supplies heated fluid through the heated irrigation tube 28 and out of the tip 20 of the cannula 18 via the port associated with the lumen 24. A variety of solutions that are compatible with the tissue being treated can be utilized. However, a preferred heated fluid is a saline solution. The saline solution is heated to a temperature between 98.6° F. and 250° F. This temperature defines the minimum threshold temperature of the liquid that is required to cause liquefaction of a specific substance when the heated liquid is presented to the specific substance. The heated fluid can be fed utilizing a pump mechanism or simply by the force of gravity.

A cooled solution irrigation tube 32 has one end thereof connected to the lumen 26 and an opposite end connected to an irrigation supply source 34. The irrigation supply source supplies fluid through the irrigation tube 32 and out of the tip 20 of the cannula via the port associated with the lumen 26. Once again, the preferred irrigation solution is a saline solution. The irrigation supply source is preferably mounted above the handpiece 12 so that gravity continuously feeds the irrigation solution through the irrigation tube 32 and out of the tip 20 of the cannula 18. It should be readily apparent, however, that a pump could also be used. This irrigation solution may be chilled pre-operatively or cooled intra-operatively. The preferred temperature for the cooled solution is believed to be approximately 40° F., although the optimal temperature will vary depending on the temperature of the heated solution and the configuration of the tip 20. That is, the temperatures of the solutions will vary depending on the type of tissue being liquefied. Furthermore, the tip 20 is disposable and may vary in size and shape depending upon what area of the body is being treated.

An aspiration tube 36 has one end connected to the lumen 22 and the opposite end connected to a vacuum source 37. The vacuum source 37 causes the target tissue and the saline solution to be aspirated from the surgical tissue field through the tip 20 of the cannula via the port associated with the lumen 24. It should be noted that all of the above operations are preferably controlled through a controller circuit 38.

A cooled solution is fed through the irrigation tube 32, through the lumen 26 and out the corresponding port in the tip 20 of the cannula 18. The flow from the irrigation source 34 is controlled by the surgeon in a manner well known in the art (e.g., a foot actuated flow control switch).

To carry out the present method, the tip 20 of the cannula 18 is inserted into the surgical tissue field. Heated saline solution is fed through the tube 28, through the lumen 24, and out of the tip 20. The solution should be heated to the melting point of the target tissue. Upon contact with the heated solution, the target tissue rapidly liquefies. By manipulating the temperature of the biocompatible liquid, the natural melting point of the target tissue may be taken advantage of to achieve selective liquefaction. It is because the total thermal energy input into the system is so low and because the thermal energy is liquid and in motion that selective liquefaction is achieved. Generally, most target surgical tissue has a lower melting point than non-target tissue because the non-target (or non-pathologic) tissue has greater structural integrity than target (or pathologic tissue).

The liquefied tissue and solution are aspirated through the lumen 22 and through the aspirating tube 36 when the vacuum source 37 is activated in a manner well known in the art, such as through the use of a foot pedal. The aspiration and irrigation take place simultaneously. Furthermore, it should be noted that the aspiration takes place substantially throughout the procedure. That is, it is believed that it is neither necessary nor desirable to liquefy the entire target tissue before aspirating the same. Rather, as a portion of the target tissue is liquefied by the heated solution, it is irrigated by the cooled solution and aspirated. This process continues until the entire target tissue has been liquefied and aspirated. In some systems, however, irrigation is not necessary and the liquefied tissue may be aspirated without irrigation.

The present method applies an energy source to the target tissue in order to liquefy the same. The present method differs from prior art methods in that the energy source in the present method is "wet-heat." That is, it uses the heat transfer modality of convection primarily rather than the heat transfer modalities of conduction and radiation.

In liquefaction, temperature is more influential than pressure; however, the heated solution must be "in motion" for liquefaction to occur. The present method uses a surgical device, such as a catheter or a handpiece as described above, through which solution is ejected under a minimal degree of pressure. The solution has to be "in motion" because the target tissue is liquefied by the heat transfer principle of convection. In this manner the target tissue, which may be fatty tissue, is liquefied and aspirated.

It should be noted that the concept of liquefaction also refers to "gelifaction" or "gelifying." That is, the "liquid" may be part liquid, part gel, or part vapor, as long as that liquid is of such a state of matter that can be aspirated with low pressure suction/aspiration technology. A "solid," on the other hand, is a state of matter that cannot be aspirated with the present low pressure suction/aspiration technology. Furthermore, aspiration refers to the technology of low pressure suction/aspiration, such as the procedure used in irrigation/aspiration procedures in cataract extraction. However, this does not eliminate the possibility of using higher pressure aspiration systems in some selected surgical sites.

The present method may also be used in such areas as prostatectomy, vascular atherectomy/thrombectomy, and tumor removal. Furthermore, the target tissue may be subcutaneous fat, atheromatous plaque, or a uterine fibroid. Again, the tip may be any size and shape in order to accommodate the area of the body being treated. Also, the tip, cannula, and tubes may be replaced in order to re-use the device. Chemically active facilitators may be added to the liquid that is to be heated in order to achieve additional efficaciousness of liquefaction. For example, fibrinolysin and EDTA may be used to liquify a fibrin-rich, calcium-rich atheromatous plaque. Also, a cytotoxic chemical agent may be added to the liquid in order to remove a tumor.

The apparatus of the present invention may also be used for dental procedures. As described above, the cannula is connected to a source of heated fluid where the fluid may be a continuous flow or pulsed so that heated fluid is repeatedly expressed from the tip of the cannula. For treatment of dental caries, the cannula is directed through an opening formed in dental enamel. The heated fluid is directed at diseased dentin tissue lying under the hole in the dental enamel. The fluid may be saline, disinfectant, an antibiotic, abrasive solutions, or the like. Furthermore, other chemicals may be added to the fluid. The diseased tissue of the tooth is liquefied and aspirated as discussed above. Additional application of heated fluid may be delivered to kill any residual bacteria or other microorganisms and then aspirated. Only decayed or diseased tissue and bacteria would be removed while leaving the viable hard or soft tissue, such as the healthy dental tissue, including nerve tissue, and blood vessels intact. Afterward, the hole may be filled with dental filler material typically used in such a procedure. Additional dental uses may include root canal surgery, plaque removal, calculus removal, soft tissue surgery, and teeth whitening.

EXAMPLE

Four pieces of tissue were cut from fresh bovine subcutaneous fat surrounded by muscle tissue and blood vessels. Each piece was approximately two inches by two inches by two inches. Each cube of tissue contained about 95% fat tissue and 5% muscle tissue with some obvious blood vessels present. Two cubes were placed in a control group and two cubes were placed in an experimental group. The control group cubes were taken from the refrigerator and placed in a microwave oven for two five-second intervals at a high temperature setting. This was done in order to raise the temperature of the fat tissue to approximately human body temperature. The two cubes were placed in a tray. A water pik (Teledyne Water Pik, model WP-20W) was set at a pressure setting of 5 which equates to 75 psi. The liquid shoots out at 20 pulses per second. The bolus size per pulse was 0.27 ml. Room temperature tap water was poured into the water pik well. The temperature was measured at 80° F. The tip of the water pik was placed directly on the first fat cube and the water pik was turned on. The pulsating water was exposed to the fat cube for approximately one minute. There was no discernible effect. The same procedure was carried out on the second fat cube. Again, there was no discernible effect.

The two fat cubes in the experimental group were then subjected to the same procedure as the control group with the exception that the water pik well was now filled with 120° F. tap water. Again, the water pik was turned on with the tip in the same place and was allowed to run for about one minute. In the first cube there was a tremendous effect. A 95% reduction in the mass of the cube was observed. There was no obvious effect on either the muscle tissue or on the blood vessel. There was a whitish fat liquid left in the tray. This liquid fat did not re-solidify and it readily poured out of the tray. The second fat cube was subjected to the same procedure, with the same result.

While the invention has been described in connection with the concept of liquefacation, it is not limited thereto. The invention can also be used for "cellular stripping." This is accomplished by utilizing the moving heated bicompatible fluid to "strip" off cells that are clinging to a wall. In dental applications it would include the concept of the stripping of bacterial cells that are clinging to a wall of dental tissue, for example. This would allow for the complete removal of any residual bacterial cells that would be lingering around after the diseased tissue was liquefied and aspirated. The stripped cells are not subjected to liquefaction as described above. Rather, they are simply stripped from their attachment to a wall, and then aspirated from the site by aspirating the resultant liquid "slurry" comprised of saline, or other liquid, and bacterial cells dispersed within this liquid medium.

The present invention may be embodied in other specific forms without departing from the spirit or essential attributes thereof and accordingly, reference should be made to the appended claims rather than to the foregoing specification as indicating the scope of the invention.

We claim:

1. A method for liquefying diseased dentin tissue within a body comprising the steps of:

heating a biocompatible fluid;

presenting said fluid to the diseased tissue within a surgical area so that the tissue is liquefied when contacted with said heated fluid while leaving healthy tissue intact; and aspirating said liquefied tissue.

2. The method as claimed in claim 1 wherein said fluid is saline.

3. The method as claimed in claim 1 wherein the dentin tissue is the diseased tissue lying underneath a hole formed in the enamel of a tooth.

4. The method as claimed in claim 1 wherein said heating step includes heating said fluid to a temperature at which temperature only the diseased tissue liquefies.

5. The method as claimed in claim 1 wherein said fluid is heated to a temperature between 98.6 and 250° F.

6. The method as claimed in claim 1 further including the step of adding chemical substances to the heated fluid to facilitate liquefying the diseased tissue.

7. The method as claimed in claim 1 further including the step of irrigating the surgical area while simultaneously aspirating said liquefied tissue.

8. The method of claim 1 further including the steps of irrigating the surgical area as a portion of the diseased tissue is liquefied and aspirated and repeating said presenting, irrigating, and aspirating steps until the desired amount of said diseased tissue has been liquefied and aspirated.

*9. A method of removing fat tissue from a region within a body that contains both fat tissue and other tissue, the method comprising the steps of:*

*presenting moving fluid to the tissues in the region, wherein the pressure and temperature of the fluid are such that (a) fat tissue in the region is liquefied by the fluid and (b) the other tissue in the region remains intact; and*

*aspirating the liquefied fat tissue and the fluid.*

*10. The method of claim 9, wherein the fluid comprises saline.*

*11. The method of claim 9, wherein the temperature of the fluid is about 120° F.*

*12. A method of removing fat tissue from a region within a body that contains both fat tissue and other tissue, the method comprising the steps of:*

*presenting numerous pulses of fluid to the tissues in the region, wherein the pressure and temperature of the pulses of fluid are such that (a) fat tissue in the region is liquefied by the pulses of fluid and (b) the other tissue in the region remains intact; and*

*aspirating the liquefied fat tissue and the fluid.*

*13. The method of claim 12, wherein, in the presenting step, a plurality of pulses are delivered per second.*

*14. The method of claim 12, wherein, in the presenting step, the pulses are delivered at a rate of about 20 pulses per second.*

*15. The method of claim 12, wherein, in the presenting step, each pulse contains about ¼ ml of fluid.*

*16. The method of claim 12, wherein, in the presenting step, the pulses are delivered at a pressure of about 75 psi.*

*17. The method of claim 12, wherein the fluid comprises saline.*

*18. The method of claim 12, wherein the temperature of the fluid is about 120° F.*

*19. The method of claim 18, wherein, in the presenting step, a plurality of pulses are delivered per second.*

*20. An apparatus for removing subcutaneous fat tissue from a region within a body that contains both fat tissue and other tissue, the apparatus comprising:*

*a heating element configured to heat a fluid;*

*a conduit configured to direct the fluid to the tissues in the region;*

*a pump adapted to pump the fluid through the conduit so that the fluid impinges on the tissues in the region, at a pressure and temperature that causes (a) the fat tissue in the region to be liquefied by the impinging fluid and (b) the other tissue in the region to remain intact; and*

*an aspiration tube operatively connected to a vacuum source for aspirating the liquefied fat and the fluid from the region.*

*21. The apparatus of claim 20, wherein the heated fluid is obtained by heating water contained in a reservoir to a set temperature.*

*22. The apparatus of claim 20, wherein the pump pumps the fluid by ejecting a plurality of boluses of fluid per second.*

*23. The apparatus of claim 22, wherein about 20 boluses are ejected per second.*

*24. The apparatus of claim 22, wherein each bolus contains about ¼ ml of fluid.*

*25. The apparatus of claim 20, wherein the fluid is delivered to the tissues in the region at a pressure of about 75 psi.*

*26. The apparatus of claim 20, wherein the fluid comprises saline.*

*27. The apparatus of claim 20, wherein the fluid is delivered to the tissues in the region at a temperature of about 120° F.*

*28. The apparatus of claim 27, wherein the pump pumps the fluid by ejecting a plurality of boluses of fluid per second.*

* * * * *